US00PP31376P2

(12) United States Plant Patent
Lim

(10) Patent No.: US PP31,376 P2
(45) Date of Patent: Jan. 21, 2020

(54) FLORIBUNDA SHRUB ROSE PLANT NAMED 'ALTGOLDICE'

(50) Latin Name: *Rosa hybrida*
Varietal Denomination: ALTgoldice

(71) Applicant: Altman Specialty Plants, Inc, Vista, CA (US)

(72) Inventor: Peter Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,558

(22) Filed: Nov. 30, 2018

(51) Int. Cl.
*A01H 5/02* (2018.01)
*A01H 6/74* (2018.01)

(52) U.S. Cl.
USPC ..... Plt./145
CPC ..... *A01H 6/74* (2018.05)

(58) Field of Classification Search
USPC ..... Plt./145, 134
CPC ..... A01H 5/0222
See application file for complete search history.

*Primary Examiner* — Kent L Bell
(74) *Attorney, Agent, or Firm* — Cassandra Bright

(57) ABSTRACT

A new and distinct floribunda *Rosa* cultivar named 'ALTgoldice' is disclosed, characterized by distinctive fully double golden yellow flowers with a strong, sweet fragrance. Plants are vigorous and can be grown on their own roots. Plants are dense, flower continuously and exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'ALTgoldice'.

BACKGROUND OF THE INVENTION

The new *Rosa* cultivar is a product of a planned breeding program conducted by the inventor, Peter Ping Lim. The objective of the breeding program was to produce vigorous new garden hybrid tea rose varieties for ornamental commercial applications. The cross resulting in this new variety was made during May of 2013.

The seed parent is the variety *Rosa* 'WEKvossutono', U.S. Plant Pat. No. 18,473. The pollen parent is the variety *Rosa* 'JACink', U.S. Plant Pat. No. 4,089. The new variety was selected in 2014 by the inventor in a group of seedlings resulting from the 2013 crossing, in a nursery in Vista, Calif.

At the time of this filing plants of 'ALTgoldice' have not been publicly released. The first sale is scheduled for March of 2019 in the United States. Information about the new variety was published in *American Rose Magazine* October of 2017. This publication, however, was not accompanied by any public access to plant material.

Asexual reproduction of the new cultivar has been achieved by vegetative cuttings. This was first performed at a research greenhouse in in Vista, Calif. in June 2014 and has shown that the unique features of this cultivar are stable and reproduced true to type in more than 5 successive generations.

SUMMARY OF THE INVENTION

The cultivar 'ALTgoldice' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTgoldice' These characteristics in combination distinguish 'ALTgoldice' as a new and distinct *Rosa* cultivar:

1. Vigorous plants.
2. Golden yellow petal color.
3. Dark, glossy foliage.
4. Strong, sweet fragrance.
5. Floribunda shrub rose.

Plants of the new cultivar 'ALTgoldice' are similar to plants of the seed parent, in most horticultural characteristics, however, plants of the new cultivar 'ALTgoldice' differ in the following:

1. The new variety has less petals than the seed parent.
2. Flower color of the new variety is brighter, deeper yellow than the seed parent.
3. Plants of the new variety are more vigorous than plants of the seed parent.

Plants of the new cultivar 'ALTgoldice' are similar to plants of the pollen parent in most horticultural characteristics, however, plants of the new cultivar 'ALTgoldice' differs in the following;

1. The new variety has smaller petals than the pollen parent.
2. Flower color of the new variety is golden yellow, the pollen parent has a pink flower.

COMMERCIAL COMPARISON

Plants of the new cultivar 'ALTgoldice' can be compared to the commercial variety *Rosa* 'Flower Carpet Yellow', U.S. Plant Pat. No. 10,527. These varieties are similar in most horticultural characteristics, however 'ALTgoldice' differs in the following:

1. The new variety has more petals per flower.
2. This comparator has a later blooming flower cycle.
3. Plants of this comparator are taller.

Plants of the new cultivar 'ALTgoldice' can also be compared to the variety *Rosa* 'MEISENTMIL', U.S. Plant Pat. No. 20,635. These varieties are similar in most horticultural characteristics, however 'ALTgoldice' differs in the following:

1. The new variety has more petals per flower.
3. This comparator has a flower with a white eye in the center, 'ALTgoldice' is solid golden yellow.
4. Plants of this comparator are lower growing, with a more spreading branching habit.
5. Flowers of this comparator are not fragrant, flowers of 'ALTgoldice' are fragrant.

BRIEF DESCRIPTION OF THE PHOTOGRAPH

The accompanying photograph illustrates in full color a close up of an individual flower. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ALTgoldice' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTgoldice'.

Market classification: Floribunda shrub rose.

PROPAGATION

Time to initiate roots: About 30 days at approximately 20° C.

Time to produce a rooted cutting: About 55 days at approximately 20° C.

PLANT

Age of plant described: Approximately 2 years.

Growth habit: Compact spreading.

Container size: 2 gallon.

Height: 30 cm.

Plant spread: 47 cm.

Rootstock: Own root.

Growth rate: Moderate.

Branching characteristics: Sympodial branching.

Length of primary lateral branches: 10 to 13 cm.

Diameter of lateral branches: Approximately 5 mm.

Quantity branches: About 5 main branches, 8 to 10 lateral branches per main branch.

Branches—young wood:

*Diameter.*—3 to 5 mm.

*Texture.*—Glabrous.

*Approximately density/quantity of thorns.*—Approximately 3 per linear cm.

*Color.*—Near RHS Green 138A.

Branches—old wood:

*Diameter.*—1.5 to 2.0 cm.

*Color.*—Near RHS Greyed-Green 197B.

*Texture.*—Rough thick woody striations.

*Thorns.*—Approximately density/quantity of thorns: 3 to 5 per linear cm. Color of thorns: Immature: RHS Yellow-Green 153D. Mature: Near RHS Greyed-Orange 166B. Shape: Deltoid, moderately hooked. Height: Average 4 mm. Diameter: Base near 4 mm. Tip near 2 mm.

FOLIAGE

Leaf:

*Arrangement.*—Alternate and compound.

*Quantity.*—Average 5 to 9 per main branch.

*Internode.*—Average range 1.3 to 4.0 cm.

*Average length.*—Approximately 9.0 cm.

*Average width.*—Approximately 6.5 cm.

Rachis:

*Average length.*—Approximately 5 cm.

*Average diameter.*—Approximately 0.2 cm.

*Color.*—Near RHS Green 138A.

*Texture.*—Glabrous all surfaces.

Leaflet:

*Quantity.*—5 per leaf.

*Average length.*—Approximately 4.0 cm.

*Average width.*—Approximately 3.0 cm.

*Shape of blade.*—Ovate.

*Apex.*—Acute.

*Base.*—Rounded.

*Margin.*—Serrate.

*Appearance of top surface.*—Very glossy.

*Appearance of bottom surface.*—Matte.

*Texture of top surface.*—Glabrous.

*Texture of bottom surface.*—Glabrous.

*Color.*—Young foliage upper side: Near RHS Green 139A. Young foliage under side: Near RHS Green 137C. Mature foliage upper side: Near RHS Green 139A. Mature foliage under side: Near RHS Green 138A.

*Venation.*—Type: Reticulate. Venation color upper side: Near RHS Green 137A. Venation color under side: Near RHS Green 138C.

Petiole:

*Average length.*—Approximately 2.0 cm.

*Average diameter.*—Approximately 0.2 cm.

*Color.*—Near RHS Green 137C.

*Texture.*—Glabrous.

FLOWER

Natural flowering season: Spring until Autumn.

Inflorescence type and habit: Single occurring, or sometimes 2, fully double rotate flowers.

Rate of flower opening: Approximately 4 days from bud to fully opened flower.

Flower longevity on plant: 10 to 14 days, after fully opened.

Quantity of flowers: 8 to 10 fully opened flowers and buds.

Flower size:

*Diameter.*—Approximately 7 cm.

*Height.*—Approximately 3 cm.

Peduncle:

*Length.*—3.5 cm.

*Diameter.*—0.35 cm.

*Color.*—Near RHS Green 143B.

Petals:

*Petal arrangement*.—Multiple rotate, overlapping whorls.

*Petal quantity*.—Approximately 20.

*Length*.—Average 3 cm.

*Width*.—Average 2.5 cm.

*Shape*.—Somewhat broad ovate to broad deltate.

*Margin*.—Entire.

*Apex*.—Rounded, sometimes acute.

*Base*.—Broad attenuate.

*Texture*.—Glabrous all surfaces.

Color: Petals.

*When opening*.—Upper surface: Near RHS Yellow 5B. Lower surface: Near RHS Yellow 10C.

*Fully opened*.—Upper surface: Near RHS Yellow 6B. Lower surface: Near RHS Yellow 6C.

*Fading*.—Upper surface: Near RHS Yellow 6C, 10D at base. Lower surface: Near RHS Yellow 10D.

Bud:

*Shape*.—Ovate.

*Length*.—Approximately 2 cm.

*Diameter*.—Approximately 1.5 cm.

*Color*.—Near RHS Yellow 6C.

Sepals:

*Quantity*.—5.

*Length*.—1.7 to 2.1 cm.

*Width*.—6 mm.

*Shape*.—Narrow.

*Apex*.—Apiculate.

*Margin*.—Entire.

*Color*.—Interior Surface: Near RHS Green 138C. Exterior Surface: Near RHS Green 138A.

*Texture*.—Densely and minutely pubescent upper and lower surfaces.

Receptacle:

*Length*.—1.0 cm.

*Width*.—1.1 cm.

*Shape*.—Flattened dome.

*Color*.—Near RHS Green 138A.

Fragrance: Strong, sweet fragrance.

REPRODUCTIVE ORGANS

Stamens:

*Quantity*.—Approximately 50 to 60.

*Filament length*.—Approximately 1.1 cm.

*Filament color*.—Near RHS Yellow 10D.

Anthers:

*Length*.—0.2 cm.

*Shape*.—Narrow globular.

*Color*.—Near RHS Yellow-Orange 15C.

*Pollen*.—Color: RHS Greyed-Orange N170A. Quantity: Scant.

Pistil:

*Length*.—Approximately 1.3 cm.

*Style*.—Length: Approximately 0.4 cm. Color: Near RHS Yellow 2D.

*Stigma*.—Shape: Linear. Color: Near RHS Yellow 2D. Ovary color: Near RHS Green 138B. Ovary shape: Oblong. Ovary length: Average 5 mm. Ovary diameter: Average 0.2 cm.

OTHER CHARACTERISTICS

Seeds and fruits: Not observed.

Disease/pest resistance: Good overall disease resistance to normal pests and diseases typical of garden roses. Very good resistance to blackspot diseases.

What is claimed is:

1. A new and distinct floribunda shrub rose plant named 'ALTgoldice' as herein illustrated and described.

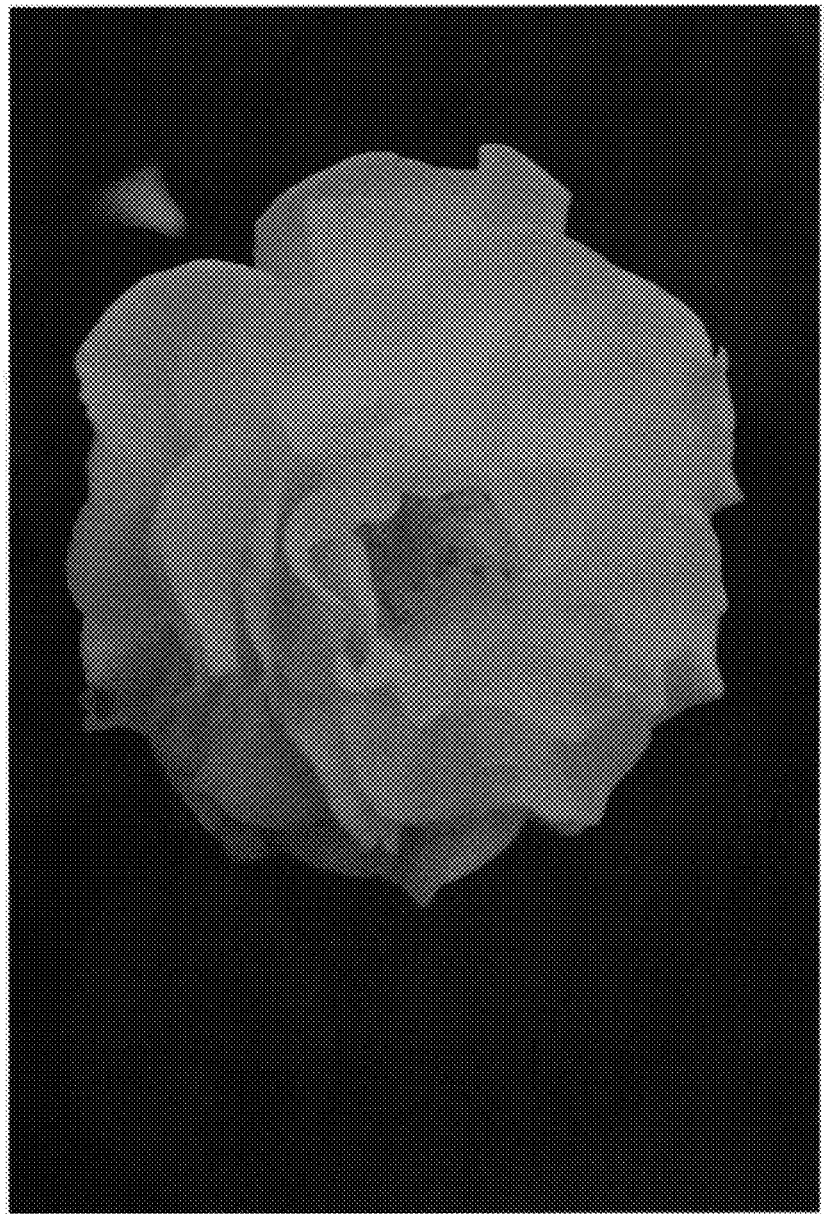

* * * * *